(12) United States Patent
Liu et al.

(10) Patent No.: US 8,901,277 B2
(45) Date of Patent: *Dec. 2, 2014

(54) INTERFERON ALPHA MUTANT AND ITS POLYETHYLENE GLYCOL DERIVATIVE

(75) Inventors: Jinyi Liu, Beijing (CN); Xiaoxia Niu, Beijing (CN); Minyi Zhou, Beijing (CN); Yi Yang, Beijing (CN); Jianbo Sun, Beijing (CN); Yongqing Cheng, Beijing (CN)

(73) Assignees: Beijing Tri-Prime Genetic Engineering Co., Ltd, Beijing (CN); Beijing Bio-Tech Development Co., Ltd., Beijing (CN)

( * ) Notice: Subject to any disclaimer, the term of this patent is extended or adjusted under 35 U.S.C. 154(b) by 275 days.

This patent is subject to a terminal disclaimer.

(21) Appl. No.: 13/431,226

(22) Filed: Mar. 27, 2012

(65) Prior Publication Data

US 2013/0287733 A1 Oct. 31, 2013

Related U.S. Application Data

(63) Continuation of application No. 12/519,917, filed as application No. PCT/CN2007/003711 on Dec. 21, 2007, now Pat. No. 8,168,751.

(30) Foreign Application Priority Data

Dec. 21, 2006 (CN) .......................... 2006 1 0167660

(51) Int. Cl.

| C07K 14/52 | (2006.01) |
|---|---|
| C12N 15/00 | (2006.01) |
| A61K 38/21 | (2006.01) |
| C07K 1/00 | (2006.01) |
| C12P 21/04 | (2006.01) |
| C07K 14/56 | (2006.01) |
| A61K 47/48 | (2006.01) |
| A61K 38/00 | (2006.01) |

(52) U.S. Cl.
CPC ........... *C07K 14/56* (2013.01); *A61K 47/48215* (2013.01); *A61K 38/00* (2013.01)
USPC ........ 530/351; 530/402; 530/421; 435/69.51; 424/85.7

(58) Field of Classification Search
None
See application file for complete search history.

(56) References Cited

U.S. PATENT DOCUMENTS

| 7,488,473 B2 | 2/2009 | Patten et al. |
| 2006/0029573 A1 | 2/2006 | Shen et al. |

FOREIGN PATENT DOCUMENTS

| CN | 1355842 A | 6/2002 |
| CN | 1511849 A | 7/2004 |
| CN | 1738640 A | 2/2006 |
| KR | 200220067105 | 8/2002 |

OTHER PUBLICATIONS

International Search Report issued in International Application No. PCT/CN2007/003711 dated Apr. 3, 2008 together with English language translation.

*Primary Examiner* — Christine J Saoud
*Assistant Examiner* — Jegatheesan Seharaseyon
(74) *Attorney, Agent, or Firm* — Scully, Scott, Murphy & Presser, P.C.

(57) ABSTRACT

IFN-alpha mutants are obtained by substituting Cys for Tyr at position 85 or 86 in existing IFN-alpha. Their polyethylene glycol derivatives with high in vitro antiviral activity and prolonged in vivo half-life are also provided, wherein a polyethylene glycol moiety is covalently bound to the free Cys residue of an IFN-alpha mutant. The preparation methods of PEG derivatives of IFN-alpha mutants and medical compositions comprising the derivatives are also provided. The test results showed that the IFN-alpha mutants of the present invention are ready to prepare and have high activity; their polyethylene glycol derivatives have extended lifetime in the body and low clearance rate.

9 Claims, 4 Drawing Sheets

SEQUENCE LISTING

```
<160> NUMBER OF SEQ ID NOS: 9

<210> SEQ ID NO 1
<211> LENGTH: 166
<212> TYPE: PRT
<213> ORGANISM: Artificial Sequence
<220> FEATURE:
<223> OTHER INFORMATION: Synthetic or recombinant polypeptide
      designated as MIFNCys86

<400> SEQUENCE: 1

Cys Asp Leu Pro Gln Thr His Ser Leu Gly Ser Arg Arg Thr Leu Ile
1               5                   10                  15

Leu Leu Ala Gln Met Arg Arg Ile Ser Pro Phe Ser Cys Leu Lys Asp
            20                  25                  30

Arg His Asp Phe Pro Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Ser
65                  70                  75                  80

Leu Leu Glu Lys Phe Cys Thr Glu Leu Tyr Gln Gln Leu Asn Asp Leu
                85                  90                  95

Glu Ala Cys Val Ile Gln Glu Val Gly Val Glu Glu Thr Pro Leu Met
```

```
                100             105                 110
Asn Val Asp Ser Ile Leu Ala Val Lys Lys Tyr Phe Gln Arg Ile Thr
            115                 120             125

Leu Tyr Leu Thr Glu Lys Lys Tyr Ser Pro Cys Ala Trp Glu Val Val
        130                 135             140

Arg Ala Glu Ile Met Arg Ser Phe Ser Leu Ser Thr Asn Leu Gln Glu
145                 150                 155                 160

Arg Leu Arg Arg Lys Asp
                165

<210> SEQ ID NO 2
<211> LENGTH: 166
<212> TYPE: PRT
<213> ORGANISM: Artificial Sequence
<220> FEATURE:
<223> OTHER INFORMATION: Synthetic or recombinant polypeptide desiganted
      as IFN-Con 1Cys86

<400> SEQUENCE: 2

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Ser
65                  70                  75                  80

Leu Leu Asp Lys Phe Cys Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Arg Leu Arg Arg Lys Asp
                165

<210> SEQ ID NO 3
<211> LENGTH: 165
<212> TYPE: PRT
<213> ORGANISM: Artificial Sequence
<220> FEATURE:
<223> OTHER INFORMATION: Syntheitc or recombinant polypeptide
      designated as IFN alpha-2aCys85

<400> SEQUENCE: 3

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
```

```
                50                  55                  60
Asn Leu Phe Ser Thr Lys Asp Ser Ser Ala Ala Trp Asp Glu Thr Leu
 65                  70                  75                  80

Leu Asp Lys Phe Cys Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
                115                 120                 125

Tyr Leu Lys Glu Lys Lys Tyr Ser Pro Cys Ala Trp Glu Val Val Arg
                130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 4
<211> LENGTH: 165
<212> TYPE: PRT
<213> ORGANISM: Artificial Sequence
<220> FEATURE:
<223> OTHER INFORMATION: Synthetic or recombinant polypeptide
      designated as IFN alpha-2bCys85

<400> SEQUENCE: 4

Cys Asp Leu Pro Gln Thr His Ser Leu Gly Ser Arg Arg Thr Leu Met
 1               5                  10                  15

Leu Leu Ala Gln Met Arg Arg Ile Ser Leu Phe Ser Cys Leu Lys Asp
                20                  25                  30

Arg His Asp Phe Gly Phe Pro Gln Glu Glu Phe Gly Asn Gln Phe Gln
                35                  40                  45

Lys Ala Glu Thr Ile Pro Val Leu His Glu Met Ile Gln Gln Ile Phe
            50                  55                  60

Asn Leu Phe Ser Thr Lys Asp Ser Ser Ala Ala Trp Asp Glu Thr Leu
 65                  70                  75                  80

Leu Asp Lys Phe Cys Thr Glu Leu Tyr Gln Gln Leu Asn Asp Leu Glu
                 85                  90                  95

Ala Cys Val Ile Gln Gly Val Gly Val Thr Glu Thr Pro Leu Met Asn
                100                 105                 110

Glu Asp Ser Ile Leu Ala Val Arg Lys Tyr Phe Gln Arg Ile Thr Leu
                115                 120                 125

Tyr Leu Lys Glu Lys Lys Tyr Ser Pro Cys Ala Trp Glu Val Val Arg
                130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 5
<211> LENGTH: 507
<212> TYPE: DNA
<213> ORGANISM: Artificial Sequence
<220> FEATURE:
<223> OTHER INFORMATION: Synthetic nucleotide sequence of MIFNCys86

<400> SEQUENCE: 5
atgtgtgacc tgccgcagac ccactctctg ggttctcgtc gtaccctgat cctgctggct    60
```

```
cagatgcgtc gtatctctcc gttctcttgc ctgaaagacc gtcacgactt cggtttcccg    120
caggaagagt tcgacggtaa ccagttccag aaagctcagg ctatctctgt tctgcacgaa    180
atgatccagc agaccttcaa cctgttctct accaaagact cttctgctgc ttgggacgaa    240
tctctgctgg aaaaattcta caccgaactg taccagcagc tgaacgacct ggaagcatgc    300
gttatccagg aagttggtgt tgaagaaacc ccgctgatga acgttgactc tatcctggtt    360
gttaaaaaat acttccagcg tatcaccctg tacctgaccg aaaaaaaata ctctccgtgt    420
gcttgggaag ttgttcgtgc tgaaatcatg cgttctttct ctctgtctac caacctgcag    480
gaacgtctgc gtcgtaaaga ctaatag                                        507

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 6
taatacgact cactataggg                                                20

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 7
gctagttatt gctcagcgg                                                 19

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 8
ggaaaaattc tgcaccgaac tgt                                            23

<210> SEQ ID NO 9
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 9
acagttcggt gcagaatttt tcc                                            23
```

INTERFERON ALPHA MUTANT AND ITS POLYETHYLENE GLYCOL DERIVATIVE

CROSS REFERENCE TO RELATED APPLICATIONS

The present application is a continuation application of U.S. patent application Ser. No. 12/519,917, filed Jun. 18, 2009, which is the National Phase of PCT/CN2007/003711 filed Dec. 21, 2007, the entire contents of which are incorporated herein by reference.

TECHNICAL FIELD

The present invention relates to preparation methods and use of IFN-alpha mutant and its polyethylene glycol derivatives. Particularly, the present invention relates to a method comprising site-directed mutagenesis of α interferon using site-directed mutagenesis technique, substituting Cys for Tyr at position 85 or 86 in IFN-alpha, and covalent binding of the site with polyethylene glycol. The present invention also relates to a method of specifically modifying interferon using Cys, extraction and purification of polyethylene glycol derivative of interferon α mutant and its use in cancer and inflammatory diseases.

BACKGROUND ART

Interferon is a type of important familial cytokine with broad-spectrum anti-virus, anti-cell proliferation and immune regulation. Interferon of mammals can be divided into interferon α, β, γ, ω, etc, wherein IFN-α can be further divided into more than ten kinds of subtypes. According to substantial clinical researches, α type interferon is an important anti-virus and anti-tumor drug. At present, there are mainly rhIFN α1b, α2a and α2b that are most widely used in clinic in China.

In addition, studies have shown that type I family of human IFN-α have more than 20 genes as its members, most of which encode functional proteins and have about 90% homology with each other at the nucleotide level. A considerable number of interferon derivatives or analogues can be produced by means of genetic engineering. At present, the most notable one is Infergen (INFERGEN®, IFN-Con 1), a wholly novel protein engineering drug, which was designed by Amgen, a United States company, based on gene sequence homology of 13 kinds of α type interferons, and approved to be listed by U.S. FDA in 1997 for the treatment of hepatitis C with anti-viral activity 5-10 times as high as interferon α2b. CN 1511849A (applicant: BEIJING TRI-PRIME GENETIC ENGINEERING CO., LTD) disclosed a variety of interferon α family molecules which were obtained by in vitro homologous recombination method and had greater advantages in activity and stability than Infergen.

However, no matter interferon α1b, α2a, α2b, or Infergen, as a protein drug, are all restricted in the clinical treatment because of poor stability, high plasma clearance, short in vivo half-life, easy to produce antigen-antibody reactions, etc. Genetic engineering techniques make large-scale synthesis of recombinant proteins become possible and greatly solve the immunogenic problems induced by heterologous proteins, but still can not overcome such disadvantages as quick plasma clearance and low bioavailability. The results of such disadvantages are as follows: frequent injections of interferon are required to achieve the effective therapeutic concentration in plasma. Moreover, after each injection greater volatility of blood concentration is caused along with formation of crest and trough value of drug concentration, thus possibly increasing the cost of treatment and the risk of drug administration inconvenience and adverse reactions. Therefore, attempts have been made to adopt a variety of drug delivery technology (Drug Delivery Technology) to enhance the efficacy of protein drugs. At present, among drug delivery technologies the most widely studied is pegylation technology (PEGNOLOGY).

Pegylation technology of protein is newly developed in the last decade for improving in vivo pharmacokinetic properties of protein-type drugs. It makes activated polyethylene glycol molecule [Poly(ethylene glycol), PEG] bonded to the surface of the protein molecules, thus affecting the spatial structure of proteins, eventually leading to changes in a variety of biochemical properties of the proteins, such as increased chemical stability, improved capacity of resistance to protease hydrolysis, reduction or disappearance of immunogenicity and toxicity, prolonged in vivo half-life, decreased plasma clearance and so on.

PEG component is an inert long-chain amphiphatic molecule generated by polymerization of ethylene monomers. Now a wide variety of PEG molecules are available. Active functional group of activated PEG can be linked to the special position of treatment molecules (such as amine, thiol or other nucleophilic substances). In most cases, covalent bonding of PEG derivatives can be achieved by using the amino group of lysine and N-terminal of peptide molecules as modification sites, each linking part determines a different isotype. During drug research and development process, PEG isotype distribution is of great significance. Because the biological activity of products has a close relation with specific isotype distribution mixtures, the products must be defined in accordance with distribution requirements. It must be proved that PEG isotype distribution is consistent during the entire drug development process including changing production process and proportional lofting. In the actual production, it brings great difficulties to process control and quality evaluation of the products.

The above trouble can be avoided by site-directed pegylation. More and more attention has been paid to pegylating specific protein sites because it can yield highly specific pegylated products and can effectively control the purity of the modified products, making the process more simple and the product quality much easier to evaluate. Highly selective pegylation of proteins can be performed by use of intramolecular cysteine (Cys) sites. There are few proteins with free sulfhydryl, but the sulfhydryl is an important covalent bond to maintain the spatial structure of proteins. Chemical modification at this site often leads to greater damage to molecular structure, thus losing protein activity. Means using genetic engineering can achieve this purpose. It is worth noting that different proteins or peptides differ in structure and property, as well as what can be introduced and where PEG modifier can be introduced. Cys artificially increased through genetic engineering means will lead to intramolecular mismatch or intermolecular combination, causing molecular instability or the formation of irregular polymer. In this regard, a comprehensive sequence analysis and accurate simulation of the molecular structure will provide a line of thought.

Sequence analysis found that the vast majority of IFN-α molecules including interferon α2a, α2b and IFN-con 1 have four cysteines, wherein there are disulfide bond formed between Cys at position 1 and 99, 29 and 139. The present applicant obtains a new type of interferon (MIFN) through in vitro homologous recombination which also maintained this characteristic. IFN-α1b and the other α family interferon obviously differ in the structure, the former has the fifth Cys at position 86 apart from the above four Cys that form normal disulfide bond. Small trial found that site-directed pegylation of interferon can be carried out by use of the site. Thus, in combination with the characteristics, pegylation of other IFN-α is expected to produce the same result.

SUMMARY OF INVENTION

The object of the present invention is to provide an interferon-α mutant. Amino acid at position 85 or 86 of its amino acid sequence is mutated to Cys which can be combined with polyethylene glycol to form a polyethylene glycol derivative with such advantages as good stability, water solubility, resistance to pathogenic as well as high biological activity.

Position 85 or 86 of IFN-α is usually tyrosine (Tyr), which locates in a relatively conservative section. The present invention modifies α interferon by mutation of Tyr to Cys and obtains a series of mutants which react with polyethylene glycol to yield a series of polyethylene glycol derivatives.

The technical solution of the present invention will be further illustrated by the following four types of α interferon commonly used at present:

$MIFN_{Cys86}$, IFN-Con $1_{Cys86}$, IFN α-$2a_{Cys85}$ and IFN α-$2b_{Cys85}$ (amino acid sequence see Appendix SEQ ID NO. 1-4), are obtained by site-directed mutagenesis of four existing interferon MIFN, IFN-Con 1, IFN α-2a and IFN α-2b and substituting Cys for the amino acid at position 86 (MIFN and IFN-Con 1) or 85 (IFN α-2a and IFN α-2b). The recombinant plasmids encoding protein are obtained by recombining target genes respectively and inserting the resulted recombinant genes into expression vector pET-23b by use of in vitro site-directed mutagenesis techniques. Separately, the four recons express efficiently and stably in *Escherichia coli* BL21 (DE3) recipient cells. The expression products exist in form of inclusion body, the expression amount accounts for more than 30% of the total bacterial protein. Followed by purification using hydrophobic interaction chromatography, DEAE anion-exchange chromatography and S-100 gel exclusion chromatography in sequence, $MIFN_{Cys86}$ and IFN-Con $1_{Cys86}$ with high purity are obtained; followed by purification using DEAE anion-exchange chromatography, monoclonal antibody affinity chromatography and S-100 gel exclusion chromatography, IFN α-$2a_{Cys85}$ and IFN α$2b_{Cys85}$ with high purity are obtained.

Even though the mutants described in the present invention are obtained by mutation of Tyr at position 85 or 86 of IFN-α to Cys, it should be understood to those skilled in the art that Tyr herein is only for illustrating the location of mutation because the chain length of IFN-α is not fully consistent. Those skilled in the art may make a variety of modification to IFN-α, for example, they may mutate some sites, thus obtaining amino acid sequences which are other than existing α interferons but have the same or similar functions with them. However, the above resulted sequences may be mutated and modified at corresponding sites described in the present invention and obtain improved performances. Thus, the IFN-α mutants of the present invention also include these sequences.

The present invention provides a variety of interferon-α mutant polyethylene glycol derivatives, wherein polyethylene glycol may be straight chain, can also have a branch structure. IFN-α mutant was pegylated with 5000~40000 Dalton of the PEG, the results showed that half-life of pegylated protein extended to various degree with increased PEG molecular weight.

The present invention also provides preparation and purification methods of interferon-α mutant polyethylene glycol derivatives.

Finally, the present invention provides in vitro pharmacodynamic and pharmacokinetic testing methods and results of interferon-α mutant polyethylene glycol derivatives, indicating that they have better technical parameters when used for treatment or prevention of immunomodulatory disorders such as tumor diseases or infectious diseases.

SPECIFIC MODE OF CARRYING OUT THE INVENTION

Figure 1:
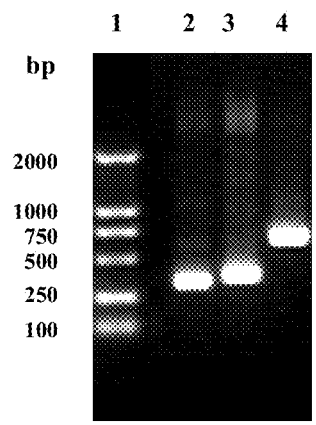
FIG. 1 denotes agarose electrophoretogram of two rounds of PCR product in "construction and amplification of the gene of $MIFN_{Cys86}$" (Example 1A). Lane 1 represents the DNA marker; lane 2 represents product of reaction system 1 in the first round of PCR reaction system; lane 3 represents product of reaction system 2 in the first round of PCR; lane 4 represents the second round of PCR product.

The present invention will be further illustrated in combination with specific examples. It should be understood that these examples are only intended to explain the present invention without limiting the scope of protection of the invention. Unless defined in particular, the terms as used herein correspond to terms well known in the related technical art. Standard chemical symbols and abbreviation symbols can be used interchangeably with the full name. For example, "PEG" and "polyethylene glycol" have the same meaning; "interferon α", "IFN-α" and "α interferon" also bear the same meaning.

Unless otherwise specified, technologies and methods as used herein but not explicitly or simply illustrated, which refer to technologies and methods conventionally used in the art, can be carried out in accordance with technologies and methods well known used in the art. Application of kits is performed in accordance with the instruction provided by producer or supplier.

In the present invention, the analogs of four proteins including MIFN, IFN-Con 1, IFN α-2a and IFN α-2b can be obtained by substitution, addition or deletion of functionally equivalent molecules of amino acid. For example, it is well known in the art to substitute one or more amino acid residue with similar properties for the corresponding amino acid residue in the original sequence, thus changing the original protein sequence to form silent change.

In the present invention, it is well known to those skilled in the art that polyethylene glycol moiety in the polyethylene glycol derivatives can have a straight-chain or branch structure. The said polyethylene glycol derivatives are pegylated reagents that can perform sulfhydryl reaction and react with sulfhydryl of cysteine residues, including maleimide-PEG, vinyl sulfone-PEG, iodo-acetamide-PEG and n-pyridyl disulfide—PEG and so on, preferably, maleimide-PEG. It has been tried in the invention to perform pegylation of four IFN-α mutants with PEG having molecular weight of about 5000, 10000, 12000, 20000, 30000 and 40,000 Dalton, and obtain derivatives of PEG-interferon respectively. Data obtained showed that half-life of pegylated proteins increased to varying extents as PEG molecular weight grew. In the Examples of the present invention, production, purification methods and pharmacodynatic, pharmacokinetic tests of PEGylated interferon derivatives are specifically illustrated using pegylated reagents with molecular weight of 20000 and 40000 Dalton as low and high molecular weight representatives respectively.

In the preferred examples, PEG reagents are mPEG-MAL [also written as PEG-MAL(20 KD)] or mPEG$_2$-MAL[also written as PEG-MAL(40 KD)] provided by Nektar Therapeutics and BEIJING JenKem Technology CO., LTD., sometimes, mPEG-MAL and mPEG$_2$-MAL as used herein are generally abbreviated to PEG-MAL or PEG.

In the present invention, engineering bacteria of four α interferon including MIFN, IFN-Con 1, IFN α-2a and IFN α-2b were provided by BEIJIGN TRI-PRIME GENETIC ENGINEERING CO., LTD. Name of the corresponding bacteria were BL21(DE3)/pET23b-MIFN, BL21(DE3)/pET23b-IFN-Con 1, BL21(DE3)/pET23b-IFN α-2a, BL21 (DE3)/pET23b-IFN α-2b.

EXAMPLE 1A

Construction and Amplification of Genes Encoding MIFN$_{Cys86}$

Using PCR in vitro site-directed mutagenesis technology (PCR-SDM), site-directed mutagenesis could be performed by means of the overlap extension. Site-directed mutagenesis technology had been mature and had a fixed procedure. What could be adjusted in accordance with a specific test was the position length of primer and PCR reaction conditions. In practice there were a variety of combinations that could achieve the purpose of site-directed mutagenesis, which were covered within the scope of protection of the invention. The present example sets forth a preferred embodiment (similarly, examples 1B~1D also set forth preferred embodiments).

Two pairs of primers were designed, the upstream primer P1 was T7 promoter primer (taatacgactcactataggg (SEQ ID NO: 6)), P3 sequence was ggaaaaattctgcaccgaactgt (SEQ ID NO: 8); downstream primer P2 was T7 terminator primer (gctagttattgctcagcgg (SEQ ID NO: 7)), P4 sequence was acagttcggtgcagaattttcc (SEQ ID NO: 9). The mutant site was contained in P3 and P4.

The plasmids of MIFN were extracted as a template, the first round of PCR included two reaction systems: the reaction system 1 included primers P 1, P4, which amplified mutation site and its upstream DNA sequence; reaction system 2 included primers P2, P3, which amplified mutation site and its downstream DNA sequence. Reaction conditions were as follows: 94° C. 4 min, 94° C. 1 min, then 55° C. 2 min, 72° C. 2 min, with 30 cycles in total. The second round of PCR was overlap extension PCR, taking the first round of PCR products as a template and taking P1, P2 as primers for PCR amplification. Reaction conditions were as follows: 94° C. 4 min, 94° C. 1 min, then 56° C. 2 min, 72° C. 2 min, with 30 cycles in total. FIG. 1 denotes agarose electrophoretogram of the two rounds of PCR products.

Products of the second round PCR were assayed by agarose electrophoresis. After double digestion of chosen DNA fragments with about 720 bp with Nde I/EcoR I, target DNA fragments with about 500 bp were recovered using electrophoresis for reserve.

EXAMPLE 1B

Construction and Amplification of Genes Encoding IFN-Con $1_{Cys86}$

Two pairs of primers were designed, the upstream primer P1 was T7 promoter primer (taatacgactcactataggg (SEQ ID NO: 6)), P3 sequence was ggaaaaattctgcaccgaactgt (SEQ ID NO: 8); downstream primer P2 was T7 terminator primer (gctagttattgctcagcgg (SEQ ID NO: 7)), P4 sequence was acagttcggtgcagaattttcc (SEQ ID NO: 9). The mutant site was contained in P3 and P4.

PCR procedure was similar to Example 1A except that reaction template of the first round of PCR was the plasmids of IFN-Con 1. Products of The second round PCR were assayed by agarose electrophoresis. After double digestion of chosen DNA fragments with about 720 bp with Nde I/EcoR I, target DNA fragments with about 500 bp were recovered using electrophoresis for reserve.

EXAMPLE 1C

Construction and Amplification of Genes Encoding IFN α-2a$_{Cys85}$

The design of primers was similar to Example 1B. PCR procedure was similar to Example 1A except that reaction template of the first round of PCR was the plasmids of IFN α-2a. Products of the second round PCR were assayed by agarose electrophoresis. After double digestion of chosen DNA fragments with about 720 bp with Nde I/EcoR I, target DNA fragments with about 500 bp were recovered using electrophoresis for reserve.

EXAMPLE 1D

Construction and Amplification of Genes Encoding IFN α-2b$_{Cys85}$

The design of primers was similar to Example 1B. PCR procedure was similar to Example 1A except that reaction template of the first round of PCR was the plasmids of IFN α-2b. Products of the second round PCR were assayed by agarose electrophoresis. After double digestion of chosen DNA fragments with about 720 bp with Nde I/EcoR I, target DNA fragments with about 500 bp were recovered using electrophoresis for reserve.

EXAMPLE 2A

Construction, Transformation and Identification of the Recombinant Plasmid of MIFN$_{Cys86}$ In the construction and transformation of plasmids, the construction of recombinant plasmids could be completed by using many kinds of restriction enzymes and adopting variable conditions of ligation reaction; in the present example, JM109 and DH5α commonly used in the laboratory were chosen as host cells, which did not exclude the use of other host for transformation. Based on the principles of science, convenience and efficiency, the embodiments of the construction, transformation, and identification of recombinant plasmids set forth in the present example were preferred (similarly, the embodiments set forth in 2B~2D were preferred).

After double digestion with Nde I/EcoR I, the plasmid vector pET-23b was recovered by agarose gel electrophoresis and ligated with the target DNA fragment from the last recovery in Example 1A. Ligated reaction conditions: 2× Rapid buffer 4~5 μl, T4 DNA Ligase 1 μl, target fragment 1~2 μl, vector 3 μl, 4° C. overnight ligation.

JM109 or DH5α competent cells were prepared and transformed with the above-mentioned ligation products, coated on the benzyl ammonia plate, and cultivated at 37° C. overnight.

Figure 2:
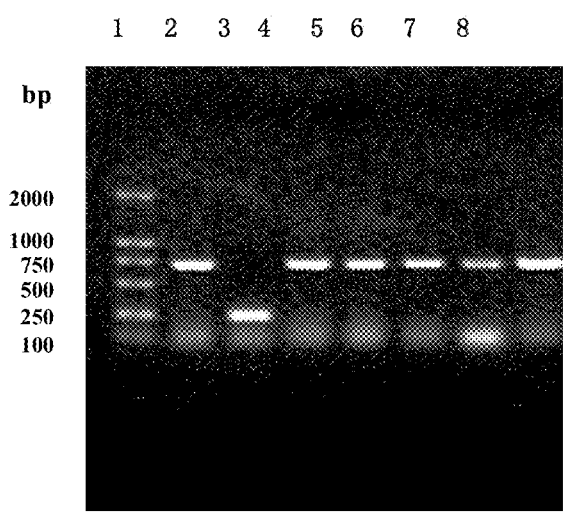
FIG. 2 denotes agarose electrophoretogram of PCR product with positive clones as a template in "construction, transformation and identification of MIFNCys86 recombinant plasmid" (Example 2A). Lane 1 represents the DNA marker; lanes 2~8 respectively represent PCR product of a single colony, wherein 2, 4, 5, 6, 7 are positive clones.
Figure 3:
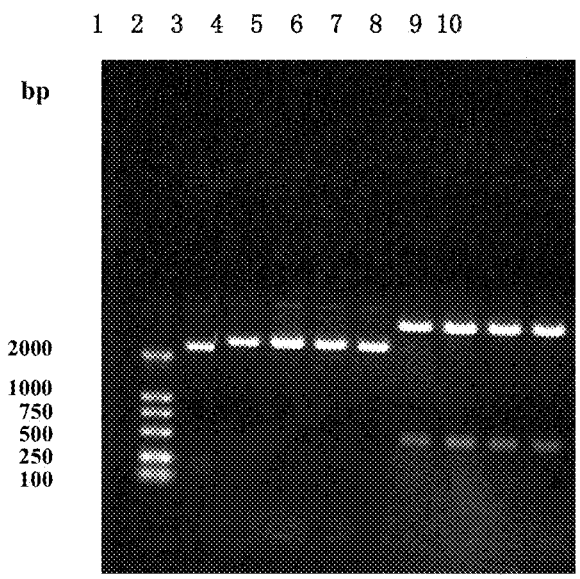
FIG. 3 denotes Nde I/EcoR I double digestion electrophoretogram of four mutant recombinant plasmids (Example 2A~2D). Lane 1 represents the DNA marker; lane 2 represents the plasmid vector pET-23b; lanes 3, 7 represent the recombinant plasmids of $MIFN_{Cys86}$ before and after digest with Nde I/EcoR I respectively; lanes 4, 8 represent the recombinant plasmids of IFN-Con $1_{Cys86}$ before and after digest with Nde I/EcoR I respectively; lanes 5, 9 represent the recombinant plasmids of IFN α-$2a_{Cys85}$ before and after digest with Nde I/EcoR I respectively; lanes 6, 10 represent the recombinant plasmids of IFN α-$2b_{Cys85}$ before and after digest with Nde I/EcoR I respectively.

Pick a single colony as a template. Primers P1, P2 designed in Example 1 were used for PCR amplification, after agarose electrophoresis of PCR products (electrophoretogram is shown in FIG. 2), specific band occurred at about 720 bp for positive clones. After cultivation a small amount of positive clones, extraction of plasmids from them and double digestion with Nde I/EcoR I, specific bands occurred at about 3 kb and 500 bp respectively (agarose electrophoretogram was shown in FIG. 3), which accords with the expected and preliminarily illustrates the success of construction of the recombinant plasmids. In order to further confirm its sequence, the automatic sequencer ABI377 was used to perform sequencing with T7 as a universal primer, the results showed that the obtained sequence was consistent with the target sequence.

EXAMPLE 2B

Construction, Transformation and Identification of the Recombinant Plasmid of IFN-Con 1$_{Cys86}$ The genetic fragments ligated in the present example were the target genetic fragments recovered in Example 1B. The technologies and methods used in the operation of ligation, transformation and identification were the same as those used in Example 2A. Electrophoretogram for identification of Nde I/EcoR digestion was shown in FIG. 3. Similarly, in order to further confirm its sequence, the automatic sequencer ABI377 was used to perform sequencing with T7 as a universal primer, the results showed that the obtained sequence is consistent with the target sequence.

EXAMPLE 2C

Construction, Transformation and Identification of the Recombinant of Plasmid IFN α-2a$_{Cys85}$ The genetic fragments ligated in the present example were the target genetic fragments recovered in Example 1C. The technologies and methods used in the operation of ligation, transformation and identification were the same as those used in Example 2A. Electrophoretogram for identification of Nde I/EcoR digestion was shown in FIG. 3. Similarly, in order to further confirm its sequence, the automatic sequencer ABI377 was used to perform sequencing with T7 as a universal primer, the results showed that the obtained sequence is consistent with the target sequence.

EXAMPLE 2D

Construction, Transformation and Identification of the Recombinant Plasmid IFN α-2bCys85

The genetic fragments ligated in the present example were the target genetic fragments recovered in Example 1D. The technologies and methods used in the operation of ligation, transformation and identification are the same as those used in Example 2A. Electrophoretogram for identification of Nde I/EcoR digestion was shown in FIG. 3. Similarly, in order to further confirm its sequence, the automatic sequencer ABI377 was used to perform sequencing with T7 as a universal primer, the results showed that the obtained sequence is consistent with the target sequence.

Example 3A

Expression and Purification of MIFN$_{Cys86}$

The recombinant plasmids obtained from Example 2A were transformed into E. coli BL21(DE3) or other suitable hosts, followed by induction expression. The expressed MIFN$_{Cys86}$ with E. coli BL21(DE3) as host, which mainly existed in the form of inclusion bodies, accounted for 30~50% of the total bacteria protein.

Rough purification: the collected bacteria were dissolved with TE. After ultrasonication, the inclusion bodies were collected, and then dissolved with 6~8 mol/L of Gu.HCl or urea, stirred at room temperature or kept at 4° C. overnight and renatured with 0.05~0.2 mol/L boric acid, pH8.0-10.5 solution. The renatured solution was kept at 4° C. overnight. After centrifugation at 4° C., the supernatant were collected, which was roughly pure MIFN$_{Cys86}$.

Figure 4:
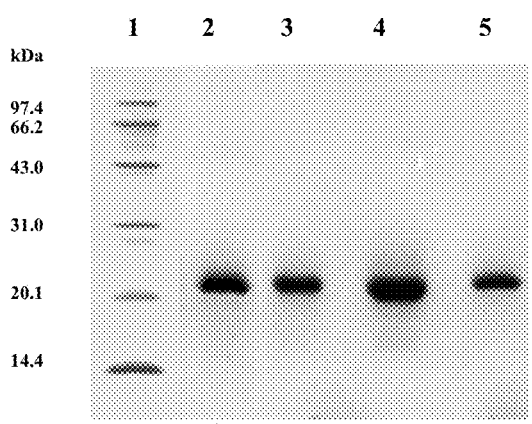
FIG. 4 denotes SDS-PAGE diagram of purified $MIFN_{Cys86}$, IFN-Con $1_{Cys86}$, IFN α-$2a_{Cys85}$ and IFN α-$2b_{Cys85}$ (Example 3A ~3D). Lane 1 represents for the protein marker; lanes 2, 3, 4, 5 represent purified $MIFN_{Cys86}$, IFN-Con $1_{Cys86}$, IFN α-$2a_{Cys85}$ and IFN α-$2b_{Cys85}$.

Fine purification: three-step purification process, which included hydrophobic chromatography, DEAE anion-exchange chromatography and S-100 gel exclusion chromatography, were employed in sequence. The detailed steps were as follows:

The renatured solution was diluted into the solution containing 10%~30% (NH$_4$)$_2$SO$_4$, loaded to Phenyl Sepharose chromatography column, washed with two column volumes of 10%~30% (NH$_4$)$_2$SO$_4$ and then eluted with 15%~35% glycol ethylene before the collected eluting peak ingredients was fully dialyzed with solution A(10~80 mmol/L Tris-HCl pH7.5~10.5); The dialyzed eluate was loaded to DEAE Sepharose FF chromatography column which was fully balanced with solution A, then eluted with solution B(solution A containing 0.2~0.4 mol/L NaCl) and the eluting peak was collected; The eluting peak fraction of DEAE Sepharose FF ion-exchange chromatography were loaded to Sephacryl S-100 chromatography column fully which was fully balanced with solution C(20~40 mmol/L PB+20~40 mmol/L NaCl Ph6.5~7.5), washed with solution C before the eluting peak was collected. After the above procedures of purification, the resulted MIFN$_{Cys86}$ had a purity of over 95% (SDS-PAGE diagram was shown in FIG. 4).

EXAMPLE 3B

Expression and Purification of IFN-Con $1_{Cys86}$

The recombinant plasmids obtained from Example 2B were transformed into *E. coli* BL21(DE3) or other suitable hosts, followed by induction expression. The expressed IFN-Con $1_{Cys86}$ with *E. coli* BL21(DE3) as host, which mainly existed in the form of inclusion bodies, accounted for 30~50% of the total bacteria protein.

The purification method in the present example was the same as that used in Example 3A. The resulted IFN-Con $1_{Cys86}$ had a purity of over 95% (SDS-PAGE diagram was shown in FIG. 4).

EXAMPLE 3C

Expression and Purification of IFN α-2a$_{Cys85}$

The recombinant plasmids obtained from Example 2C were transformed into *E. coli* BL21(DE3) or other suitable hosts, followed by induction expression. The expressed IFN-Con $1_{Cys86}$ with *E. coli* BL21(DE3) as host, which mainly existed in the form of inclusion bodies, accounted for 30~50% of the total bacteria protein.

Rough purification: the roughly purified method in the present example was the same as that used in Example 3A.

Fine purification: three-step purification process, which included hydrophobic chromatography, DEAE anion-exchange chromatography and S-100 gel exclusion chromatography, were employed in sequence. The detailed steps were as follows:

The renatured solution was diluted 10 times with 30 mmol/L Tris-HCl (pH8.0), then loaded to DEAE Sepharose FF ion-exchange chromatography column and eluted with 30 mmol/L Tris-HCl (pH7.0) solution containing 0.3 mol/L of NaCl before the eluting peak was collected; the eluted sample from the above step was diluted three-times with PBS (pH7.0), then loaded to IFN α-2a monoclonal antibody affinity chromatography column and eluted with 0.3 mol/L Gly solution(pH 2.5) containing 100 mmol/L of NaCl before the eluting peak was collected; then the eluted sample from the above step was loaded to Sephacryl S-100 chromatography column and eluted with PBS(pH7.0). The resulted IFN α-2a$_{Cys85}$ had a purity of over 95% (SDS-PAGE diagram was shown in FIG. 4).

EXAMPLE 3D

Expression and Purification of IFN α-2b$_{Cys85}$

The recombinant plasmids obtained from example 2D were transformed into *E. coli* BL21(DE3) or other suitable hosts, followed by induction expression. The expressed IFN α-2b$_{Cys85}$ with *E. coli* BL21(DE3) as host, which mainly existed in the form of inclusion bodies, accounted for 30~50% of the total bacteria protein.

Rough purification: the roughly purified method in the present example was the same as that used in Example 3A.

Fine purification: three-step purification process, which included hydrophobic chromatography, DEAE anion-exchange chromatography and S-100 gel exclusion chromatography, were employed in sequence. The specific steps were as follows:

The renatured solution was diluted 10 times with 30 mmol/L Tris-HCl (pH8.0), then loaded to DEAE Sepharose FF ion-exchange chromatography column and eluted with 30 mmol/L Tris-HCl (pH7.0) solution containing 0.3 mol/L of NaCl before the eluting peak was collected; the eluted sample from the above step was diluted three-times with PBS (pH7.0), then loaded to IFN α-2b monoclonal antibody affinity chromatography column and eluted with 0.3 mol/L Gly solution containing 100 mmol/L of NaCl before the eluting peak was collected; then the eluted sample from the above step was loaded to Sephacryl S-100 chromatography column and eluted with PBS (pH7.0). The resulted IFN α-2b$_{Cys85}$ had a purity of over 95% (SDS-PAGE diagram was shown in FIG. 4).

EXAMPLE 4

PEG Coupling of MIFN$_{Cys86}$, IFN-Con $1_{Cys86}$, IFN α-2a$_{Cys85}$ and IFN α-2b$_{Cys85}$ In the present invention, four mutants of interferon α could be coupled with PEG having a variety of molecular weight. In preferred examples, PEG included mPEG-MAL and mPEG$_2$-MAL with molecular weight of approximately 20 KD and 40 KD respectively.

1) Concentration of MIFN$_{Cys86}$, IFN-Con $1_{Cys86}$, IFN α-2a$_{Cys85}$ and IFN α-2b$_{Cys85}$ The above four interferon α mutants may be concentrated respectively by DEAE Sepharose FF chromatography column. The specific method was as follows: the purified protein sample obtained from any one of Examples 3A ~3D was diluted two-time or more with a solution of 10~80 mmol/L Tris-HCl, pH7.5~8.5, loaded to DEAE chromatography column and then eluted with 20 mmol/L PB buffer (pH 7.6)+300 mmol/L NaCl to get the concentrated solution of target protein.

2) Coupling of MIFN$_{Cys86}$, IFN-Con $1_{Cys86}$, IFN α-2a$_{Cys85}$ and IFN α-2b$_{Cys85}$ with mPEG-MAL MIFN$_{Cys86}$, IFN-Con $1_{Cys86}$, IFN α-2a$_{Cys85}$ and IFN α-2b$_{Cys85}$ was coupled with mPEG(20 KD)-MAL, the monopegylated derivatives, respectively, so write: mPEG(20 KD)-MIFN$_{Cys86}$, mPEG(20 KD)-IFN-Con $1_{Cys86}$, mPEG(20 KD)-IFN α-2a$_{Cys85}$ and mPEG(20 KD)-IFN α-2b$_{Cys85}$.

MIFN$_{Cys86}$, IFN-Con $1_{Cys86}$, IFN α-2a$_{Cys85}$ and IFN α-2b$_{Cys85}$ was coupled with mPEG(40 KD)-MAL, the monopegylated derivatives, respectively, so write: mPEG(40 KD)-MIFN$_{Cys86}$, mPEG(40 KD)-IFN-Con $1_{Cys86}$, mPEG(40 KD)-IFN α-2a$_{Cys85}$ and mPEG(40 KD)-IFN α-2b$_{Cys85}$.

Figure 5:
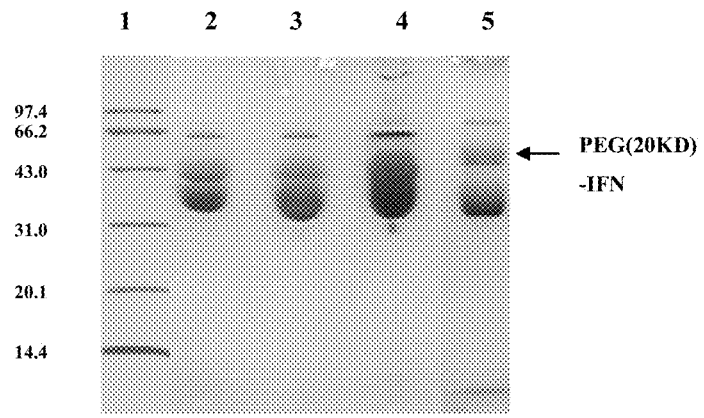
FIG. 5 denotes SDS-PAGE diagram of ligation reaction performed by $MIFN_{Cys86}$, IFN-Con $1_{Cys86}$, IFN α-$2a_{Cys85}$ and IFN α-$2b_{Cys85}$ With PEG-MAL(20 KD) (Example 4). Lane 1 represent the protein marker; lanes 2, 3, 4, 5 respectively represent products of ligation reaction performed by $MIFN_{Cys86}$, IFN-Con $1_{Cys86}$, IFN α-$2a_{Cys85}$ and α-$2b_{Cys85}$ with PEG-MAL(20 KD).
Figure 6:
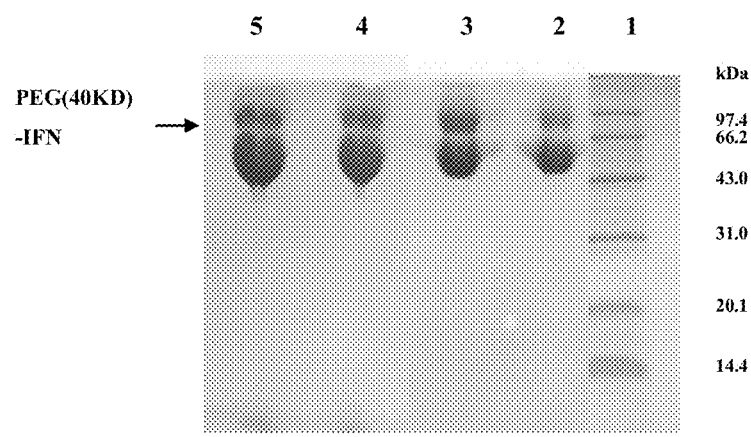
FIG. 6 denotes SDS-PAGE diagram of ligation reaction performed by $MIFN_{Cys86}$, IFN-Con $1_{Cys86}$, IFN α-$2a_{Cys85}$ and IFN α-$2b_{Cys85}$ with PEG-MAL(40 KD) (Example 4). Lane 1 represents the protein marker; lanes 2, 3, 4, 5 respectively represent products of ligation reaction performed by $MIFN_{Cys86}$, IFN-Con $1_{Cys86}$, IFN α-$2a_{Cys85}$ and IFN α-$2b_{Cys85}$ with PEG-MAL(40 KD).

The coupling reaction had the specific steps as follows:

Moderate volume of concentrated solution was taken from the step 1) of the present invention, and adjusted to 8~12 mg/ml for protein concentration. The PEG powder was added with a molar ratio of 1:1, gently shaken, so that it could dissolve before reacting at 4° C. overnight, that was, reaction time should be more than 10 hours. SDS-PAGE detected the degree of coupling reaction (as shown in FIG. 5-6).

EXAMPLE 5

Purification of Interferon-α Mutant Derivatives

Figure 7:
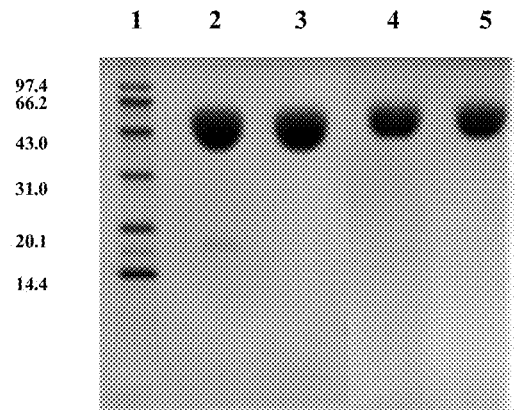
FIG. 7 denotes SDS-PAGE diagram of four kinds of purified PEG-MAL (20 KD) derivatives of interferon-α mutants (Example 5). Lane 1 represents for the protein marker; Lanes 2, 3, 4, 5 respectively represent mPEG(20 KD)-$MIFN_{Cys86}$, mPEG(20 KD)-IFN-Con $1_{Cys86}$, mPEG(20 KD)-IFN α-$2a_{Cys85}$ and mPEG(20 KD)-IFN α-$2b_{Cys85}$.
Figure 8:
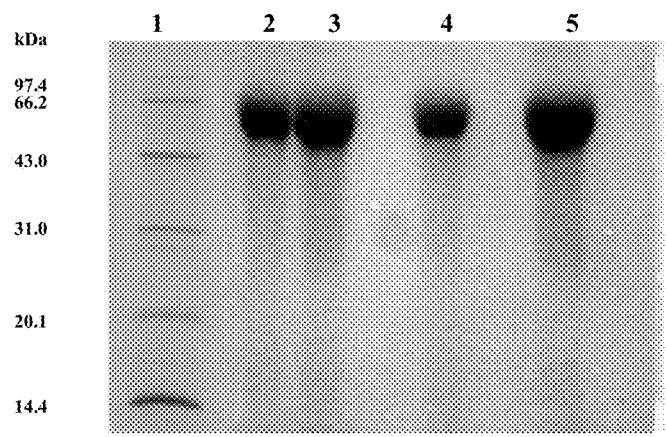
FIG. 8 denotes SDS-PAGE diagram of four kinds of purified PEG-MAL (40 KD) derivatives of interferon-α mutants (Example 5). Lane 1 represents the protein marker; Lanes 2, 3, 4, 5 respectively represent mPEG(40 KD)-$MIFN_{Cys86}$, mPEG(40 KD)-IFN-Con $1_{Cys86}$, mPEG(40 KD)-IFN α-2a$_{Cys85}$ and mPEG(40 KD)-IFN α-2b$_{Cys85}$.

The pegylated products were purified by DEAE Sepharose Fast Flow ion-exchange chromatography, the specific conditions were as follows: reaction solution was diluted 20 to 30 times using 25 mmol pH8.0 Tris buffer system, then loaded to balanced DEAE column with a flow rate of 3~4 ml/min, and after baseline balanced, eluted with NaCl concentration of 80 mM in 25 mM pH 8.0 Tris to obtain the elution peak of target protein. Final purity of the resulted recombinant protein was over 95% (SDS-PAGE diagram were shown in FIGS. 7-8).

EXAMPLE 6

Determination of In Vitro Antiviral Activity of Four Kinds of Interferon α, Mutants and Polyethylene Glycol Derivatives of Mutants Thereof Cytopathic effect inhibition assay using WISH-VSV system was adopted to determine interferon antiviral activity in vitro, which was the method well known to the public in prior art. The specific reference was shown in Appendix 3 XC "Determination of biological activity of interferon", 2005 edition of "People's Republic of China Pharmacopoeia".

In the present example, 16 interferons (or derivatives) were determined for in vitro antiviral activity, including in detail:

Four kinds of interferon α: MIFN, IFN-Con 1, IFN α-2a and IFN α-2b;

Four kinds of mutants of IFN-α: $MIFN_{Cys86}$, $IFN\text{-}Con\ 1_{Cys86}$, $IFN\ \alpha\text{-}2a_{Cys85}$ and $IFN\ \alpha\text{-}2b_{Cys85}$ (prepared by Examples 3A~3D in the present invention);

Also, there were eight kinds of polyethylene glycol derivatives: $mPEG(20\ KD)\text{-}MIFN_{Cys86}$, $mPEG(20\ KD)\text{-}IFN\text{-}Con\ 1_{Cys86}$, $mPEG(20\ KD)\text{-}IFN\ \alpha\text{-}2a_{Cys85}$, $mPEG(20\ KD)\text{-}IFN\ \alpha\text{-}2a_{Cys85}$, $mPEG(40\ KD)\text{-}MIFN_{Cys86}$, $mPEG(40\ KD)\text{-}IFN\text{-}Con\ 1_{Cys86}$, $mPEG(40KD)\text{-}IFN\ \alpha\text{-}2a_{Cys85}$ and $mPEG(40\ KD)\text{-}IFN\ \alpha\text{-}2b_{Cys85}$ (prepared by Example 5 in the present invention).

Their in vitro anti-viral activity assay results were shown in the following Table 1~4.

TABLE 1

In vitro antiviral activity of MIFN, $MIFN_{Cys86}$, $mPEG(20KD)\text{-}MIFN_{Cys86}$ and $mPEG(40KD)\text{-}MIFN_{Cys86}$

| name | specific activity(IU/mg) | Retention activity (%) |
|---|---|---|
| MIFN | $5.57 \pm 0.38 \times 10^8$ | — |
| $MIFN_{Cys86}$ | $5.68 \pm 0.29 \times 10^8$ | 100 |
| $mPEG(20KD)\text{-}MIFN_{Cys86}$ | $5.84 \pm 0.35 \times 10^6$ | 1.03 |
| $mPEG(40KD)\text{-}MIFN_{Cys86}$ | $4.12 \pm 0.31 \times 10^6$ | 0.73 |

TABLE 2

In vitro anti-viral activity of IFN-Con 1, $IFN\text{-}Con\ 1_{Cys86}$, $mPEG(20KD)\text{-}IFN\text{-}Con\ 1_{Cys86}$ and $mPEG(40KD)\text{-}IFN\text{-}Con\ 1_{Cys86}$

| name | specific activity (IU/mg) | Retention activity (%) |
|---|---|---|
| IFN-Con 1 | $5.18 \pm 0.24 \times 10^8$ | — |
| $IFN\text{-}Con\ 1_{Cys86}$ | $5.13 \pm 0.30 \times 10^8$ | 100 |
| $mPEG(20KD)\text{-}IFN\text{-}Con\ 1_{Cys86}$ | $5.24 \pm 0.27 \times 10^6$ | 1.02 |
| $mPEG(40KD)\text{-}IFN\text{-}Con\ 1_{Cys86}$ | $4.05 \pm 0.25 \times 10^6$ | 0.79 |

TABLE 3

In vitro anti-viral activity of IFN α-2a, $IFN\ \alpha\text{-}2a_{Cys85}$, $mPEG(20KD)\text{-}IFN\ \alpha\text{-}2a_{Cys85}$ and $mPEG(40KD)\text{-}IFN\ \alpha\text{-}2a_{Cys85}$

| name | specific activity(IU/mg) | Retention activity (%) |
|---|---|---|
| IFN α-2a | $1.09 \pm 0.20 \times 10^8$ | — |
| $IFN\ \alpha\text{-}2a_{Cys85}$ | $1.06 \pm 0.23 \times 10^8$ | 100 |
| $mPEG(20KD)\text{-}IFN\ \alpha\text{-}2a_{Cys85}$ | $1.79 \pm 0.30 \times 10^6$ | 1.69 |
| $mPEG(40KD)\text{-}IFN\ \alpha\text{-}2a_{Cys85}$ | $1.28 \pm 0.21 \times 10^6$ | 1.21 |

TABLE 4

In vitro anti-viral activity of IFN α-2b, $IFN\ \alpha\text{-}2b_{Cys85}$, $mPEG(20KD)\text{-}IFN\ \alpha\text{-}2b_{Cys85}$ and $mPEG(40KD)\text{-}IFN\ \alpha\text{-}2b_{Cys85}$

| name | specific activity(IU/mg) | Retention activity (%) |
|---|---|---|
| IFN α-2b | $1.10 \pm 0.20 \times 10^8$ | — |
| $IFN\ \alpha\text{-}2b_{Cys85}$ | $1.12 \pm 0.27 \times 10^8$ | 100 |
| $mPEG(20KD)\text{-}IFN\ \alpha\text{-}2b_{Cys85}$ | $1.64 \pm 0.33 \times 10^6$ | 1.46 |
| $mPEG(40KD)\text{-}IFN\ \alpha\text{-}2b_{Cys85}$ | $1.20 \pm 0.26 \times 10^6$ | 1.07 |

EXAMPLE 7

Pharmacokinetic Study of Rats

Through the pharmacokinetic scheme shown in table 5, 12 interferon (or derivatives) were determined for in vitro antiviral activity, including in detail:

Four kinds of mutants of IFN-α: $MIFN_{Cys86}$, $IFN\text{-}Con\ 1_{Cys86}$, $IFN\ \alpha\text{-}2a_{Cys85}$ and $IFN\ \alpha\text{-}2b_{Cys85}$ (prepared by Examples 3A~3D in the present invention); Eight kinds of polyethylene glycol derivatives: $mPEG(20\ KD)\text{-}MIFN_{Cys86}$, $mPEG(20\ KD)\text{-}IFN\text{-}Con\ 1_{Cys86}$, $mPEG(20\ KD)\text{-}IFN\ \alpha\text{-}2a_{Cys85}$, $mPEG(20\ KD)\text{-}IFN\ \alpha\text{-}2b_{Cys85}$, $mPEG(40\ KD)\text{-}MIFN_{Cys86}$, $mPEG(40\ KD)\text{-}IFN\text{-}Con\ 1_{Cys86}$, $mPEG(40\ KD)\text{-}IFN\ \alpha\text{-}2a_{Cys85}$ and $mPEG(40\ KD)\text{-}IFN\ \alpha\text{-}2b_{Cys85}$ (prepared by Example 5 in the present invention).

TABLE 5

Pharmacokinetic scheme

| | mutants of INF-α | Pegyalted derivatives of mutants of INF-α |
|---|---|---|
| rat | 6 pieces | 6 pieces |
| administration route | subcutaneous | subcutaneous |
| administration mode | single | single |
| administration dose | 3.3 MIU | 5.4 MIU |
| time point of blood | 0, 0.2, 0.5, 0.75, 1, 2, 4, 8, 12, 16, 24 | 0, 0.5, 2, 4, 8, 12, 16, 24, 48, 72, 96, 168 |
| determination method | WISH/VSV | WISH/VSV |

In the above test scheme, the blood samples were collected from the rat's eyeround and then centrifuged to collect serum. The content of interferons in the serum sample was determined by CPE method (WISH/VSV system).

TABLE 6

Pharmacokinetic parameter table of MIFN$_{Cys86}$ and its PEG derivatives

| PK parameter | MIFN$_{Cys86}$ | mPEG (20KD)-MIFN$_{Cys86}$ | mPEG(40KD)-MIFN$_{Cys86}$ |
|---|---|---|---|
| t1/2Ka(h) | 0.25 | 15.0 | 17.1 |
| t1/2Ke(h) | 1.57 | 18.0 | 24.8 |
| Tpeak(h) | 0.78 | 24.3 | 26.5 |
| Cpeak(IU/ml) | 23823.7 | 26941.7 | 30628.6 |
| AUC(IU·h/ml) | 76230.8 | 1744758.0 | 2815579.3 |

It was found after 3P87 software fitting that the metabolism of MIFNCys86 and its PEG derivatives in SD rats was in line with a compartment model of first-order absorption. Pegylation could significantly improve the pharmacokinetic properties of MIFNCys86. Comparing with MIFN$_{Cys86}$, mPEG-MIFN$_{Cys86}$ had significantly prolonged half-life of absorption, peak time and elimination half-life, significantly increased area under drug-time curve, significantly decreased clearance rate. It can be seen that pegylation could extend the average lifetime of MIFN$_{Cys86}$ in the body and reduce the clearance rate.

The same results had been found in the pharmacokinetic tests of IFN-Con 1$_{Cys86}$ and its PEG derivatives, IFN α-2a$_{Cys85}$ and its PEG derivatives, IFN α-2b$_{Cys85}$ and its PEG derivatives, that was, Comparing with the unmodified, pegylated interferon had significantly prolonged half-life of absorption, peak time and elimination half-life, significantly increased area under drug-time curve, significantly decreased clearance rate.

Thereby it can be proved that pegylation can extend the average lifetime of interferons in the body and reduce the clearance rate.

At this point, the present invention had been carried out substantially full description. The preferred examples can only illustrate but not limit the present invention, for those in the art that certain modification and improvement may be made to the invention as described without departing from the protection scope of the invention.

INDUSTRIAL APPLICABILITY

Animal experiments showed that polyethylene glycol derivatives of interferon mutants of the present invention could extend the average lifetime of interferons in the body and reduce the clearance rate and had substantially high anti-virus activity. Thus, in accordance with the methods described in the present invention or well known to those in the art, it can be carried out to prepare interferon mutants of the present invention, followed by further covalently bound to polyethylene glycol and developed into drugs for prevention and treatment of immunoregulatory disorders such as tumor diseases or infectious diseases.

Sequence list is attached:

Attached find the sequence lists of amino acids and nucleotide, wherein the nucleotide sequences of IFN-Con 1, IFN α-2a and IFN α-2b is known to the public, in the specific examples, only the condons of corresponding sites are mutated into tgc. Therefore, the DNA sequences of IFN-Con 1$_{Cys86}$, IFN α-2a$_{Cys85}$ and IFN α-2b$_{Cys85}$ are not attached in the present invention SEQ ID NO:1 shows the amino acids sequence of MIFN-$_{Cys86}$;
SEQ ID NO:2 shows the amino acids sequence of IFN-Con 1$_{Cys86}$;
SEQ ID NO:3 shows the amino acids sequence of IFN α-2a$_{Cys85}$;
SEQ ID NO:4 shows the amino acids sequence of IFN α-2b$_{Cys85}$;
SEQ ID NO:5 shows the DNA sequence of MIFN$_{Cys86}$;
SEQ ID NO: 6~9 show the nucleotide sequences of primers P 1~P4 respectively.

What is claimed is:

1. An isolated interferon-α mutant protein comprising the amino acid sequence of SEQ ID NO: 2, 3 or 4.

2. A polyethylene glycol derivative of the interferon-α mutant protein of claim 1.

3. The polyethylene glycol derivative of the interferon-α mutant protein of claim 2, wherein a PEG reagent modifies the site of the Cys at position 85 or 86 of said interferon-α mutant protein.

4. The polyethylene glycol derivative of the interferon-α mutant protein of claim 3, wherein said derivative is obtained by reacting a polyethylene glycol sulfhydryl modifier with the Cys residue at position 85 or 86 of said interferon-α mutant, said polyethylene glycol sulfhydryl modifier being selected from the group consisting of maleimide-PEG, vinyl sulfone-PEG, iodoacetamide-PEG and n-pyridyl disulfide-PEG.

5. The polyethylene glycol derivative of the interferon-α mutant protein of claim 3, wherein the average molecular weight of said PEG reagent is 5,000 to 60,000 Daltons.

6. A method of preparing a polyethylene glycol derivative of an interferon-α mutant protein, wherein said interferon-α mutant protein comprises the amino acid sequence of SEQ ID NO: 2, 3 or 4, said method comprising:
 a) preparing a concentrated solution of an interferon-α mutant protein;
 b) coupling polyethylene glycol with said interferon-α mutant protein; and
 c) purifying and extracting a polyethylene glycol derivative of said interferon-α mutant protein.

7. A pharmaceutical composition comprising a polyethylene glycol derivative of an interferon-α mutant protein according to any one of claims 3 to 6.

8. A method for the treatment of viral infections or tumors in a subject comprising administering to said subject the pharmaceutical composition of claim 7.

9. An isolated nucleic acid, encoding the interferon-α mutant protein comprising the amino acid sequence of SEQ ID NO: 2, 3 or 4.

\* \* \* \* \*